(12) United States Patent
Laube et al.

(10) Patent No.: US 6,214,407 B1
(45) Date of Patent: Apr. 10, 2001

(54) METHOD OF SURFACE COATING MEDICAL IMPLANTS

(75) Inventors: Horst Laube; Erika Nickel; Martin Matthaeus, all of Berlin; Helmut Willenbockel, Schneverdingen, all of (DE)

(73) Assignee: co.don AG (DE)

( * ) Notice: Subject to any disclaimer, the term of this patent is extended or adjusted under 35 U.S.C. 154(b) by 0 days.

(21) Appl. No.: 09/432,497

(22) Filed: Nov. 2, 1999

(51) Int. Cl.$^7$ ........................................... A61L 27/00
(52) U.S. Cl. ................... 427/2.24; 427/2.18; 427/2.25; 427/2.28; 427/2.3; 427/242; 118/56
(58) Field of Search ................... 427/2.18, 2.24, 427/2.25, 2.28, 2.3, 242, 366; 118/56

(56) References Cited

U.S. PATENT DOCUMENTS

| | | | |
|---|---|---|---|
| 5,037,378 | * | 8/1991 | Muller et al. ........................... 600/36 |
| 5,205,867 | * | 4/1993 | Ziger ....................................... 118/54 |
| 6,060,129 | * | 5/2000 | Thomas et al. ....................... 427/490 |

FOREIGN PATENT DOCUMENTS

WO 93/01843 * 2/1993 (WO) ............................. A61L/33/00

* cited by examiner

Primary Examiner—Shrive Beck
Assistant Examiner—Jennifer Kolb
(74) Attorney, Agent, or Firm—W. F. Fasse; W. G. Fasse

(57) ABSTRACT

To coat a surface of a medical implant such as an organ part or a synthetic prosthesis with a coating of living cells, the implant is inserted and fixed into a receiving container which is at least partially filled with a nutritive liquid medium containing the coating cells in suspension. Then the receiving container is rotated respectively about two distinct rotation axes, whereby preferably the two rotation motions are independently controllable and the two axes are substantially perpendicular to each other. Each of the two rotation motions can be a continuous rotation through 360°, or a stepwise intermittent rotation through successive rotational angle steps. The parameters of the two rotations about the two axes can be combined as needed for a particular application, for example a continuous rotation about one axis combined with a stepwise rotation about the other axis. The time period and rotational speed of each rotation can also be independently controlled. A uniform and complete coating of cells on all surfaces of the implant is achieved.

23 Claims, 2 Drawing Sheets

METHOD OF SURFACE COATING MEDICAL IMPLANTS

FIELD OF THE INVENTION

The invention relates to a method of coating the surfaces of medical implants with living cells deposited from a nutritive physiological liquid, wherein the implants are placed into a receiving container which is filled with the liquid containing the cells and which is then rotated around at least one axis.

BACKGROUND INFORMATION

It is widely known to implant medical implants, which include natural biological implants such as transplanted organs or parts thereof as well as artificial prostheses, into the bodies of recipient patients. The medical implants used in this context can therefore consist of living tissue that has been harvested from living or recently deceased bodies, such as animal bodies, or of non-living, biologically inert materials. However, a medical implant that does not originate from the tissues or cells of the respective recipient patient himself or from his identical twin, will often be recognized by the recipient organism as a foreign body and will therefore be attacked and combatted by so-called immunocompetent or immunoactive cells of the immune system of the recipient patient.

In order to prevent such an immune reaction in a patient who is to receive a medical implant, it is known in the art to cover the surfaces of the implant that would otherwise be recognized as a foreign body, with a coating layer of cells taken from the patient's own body or cells of an identical character, before the implant is implanted into the patient's body. Due to the surface coating of cells that are recognized as autologous (or at least not recognized as foreign) by the recipient patient's immune system, the coated implant will not be attacked by the immune system of the patient. In other words, the coating of cells applied onto the surface of the medical implant masks the foreign characteristics of the implant material.

In the conventional coating process, the coating cells are typically applied in the manner of a cell suspension onto the implant, whether it be a natural organ, a part of an organ, or an artificial prosthesis, before the operation by which this implant is to be implanted into the recipient patient. In this context, it is the goal to ensure that as many living cells as possible are deposited out of the cell suspension onto the surface to be coated, and that these living cells remain adherently fixed on the intended surface and then grow securely in place on this surface.

The PCT International Patent Publication WO 93/01843 discloses a method of the type generally described above, which serves to coat the surfaces of cylindrical medical implants. In this known method, the tubular implants that are to be coated are inserted into a horizontally arranged cylindrical chamber, which is filled with the respective cell suspension. The chamber is then rotated about its lengthwise axis, either in a continuous rotation or in a step-wise partial rotation manner. The partial stepwise rotation involves rotating the chamber about its lengthwise axis through a prescribed rotational angle, and then holding the chamber fixed for a predetermined period of time in the particular angular position that was reached by the partial rotation, and thereafter rotating the chamber through another rotational angle and again holding the chamber fixed in the new angular position for a predetermined period of time.

SUMMARY OF THE INVENTION

In view of the above, it is an object of the invention to provide a method of applying a surface coating onto a surface of a medical implant in such a manner that the selected surfaces or all surfaces of an implant having any desired configuration can be surfacially completely and uniformly covered and populated by a coating of cells that originate from the body of the recipient patient himself or cells that are genetically identical thereto, whereby the implant may be a natural biological implant such as an organ or an artificial implant such as a synthetic prosthesis. The invention further aims to avoid or overcome the disadvantages of the prior art, and to achieve additional advantages, as apparent from the present specification.

The above objects have been achieved in a method of coating the surface of a medical implant with living cells, according to the invention, comprising the following steps: placing, or particularly inserting and fixing, the implant into a chamber of a receiving container; filling at least a portion of the chamber of the receiving container with a nutritive liquid containing living cells; and rotating the receiving container independently about two rotation axes that are preferably substantially perpendicular to each other. The rotation can be carried out simultaneously or successively about the two axes. The particular pattern or manner of rotation about each of the two rotation axes can be carried out according to a prescribed motion program or sequence.

The living cells that are used in the method according to the invention can either be cells of the recipient body, such as cells recovered from a blood vessel, part of an organ, or other tissue sample of the patient, or may be genetically altered omnipotent donor cells. The living cells are seeded into a nutritive physiological liquid or solution, and are then deposited from this liquid medium to form a coating on the medical implant that is intended to be implanted into the patient in a subsequent implantation operation. More particularly, the cells are deposited out of the liquid medium onto the respective surface or surfaces of the implant as the receiving container (together with the implant and liquid medium therein) is rotated about the two rotation axes. Due to the rotation of the receiving container about the two rotation axes, the cells are deposited onto the surface or surfaces of the implant under the influence of gravity and/or a centrifugal force generated by the rotation.

Preferably, the respective rotation is carried out simultaneously and independently about the two axes, and the two axes are substantially perpendicular to each other. Throughout this specification, unless otherwise defined, the term "substantially" means that the indicated parameter is within the customary range of accuracy and precision that is used in the present art for specifying and/or carrying out a physical embodiment of such a parameter. Due to the rotation about two distinct axes, the depositing of the cells onto the surface of the implant is especially uniform and complete, and can be controlled or targeted as desired.

An apparatus that is suitable for carrying out the method according to the invention comprises a set of different modular receiving containers, i.e. receiving containers that are assembled as needed from different modular container components, whereby the respective size of the interior chamber of the receiving container is respectively optimally adapted to the size and configuration of the implant that is to be coated. The apparatus further includes a motion unit or particularly a so-called coating rotator for rotating the receiving container. The coating rotator is embodied in such a manner that it can receive and carry a receiving container and rotate this container together with the implant contained therein, either simultaneously or separately in any desired steps or succession and with any desired rotational speeds respectively about two rotation axes that are preferably substantially perpendicular to each other. In this manner, the apparatus ensures that an absolutely uniform distribution of the cells is achieved over the surfaces of the implant, so that the resulting coating on the surfaces is complete and uniform.

The use of the inventive method contributes to a substantial improvement of the success rate of implantation operations, for example heart valve operations, because of the improved coating results. Namely, the high quality of the "masking" cell coating applied onto the implant according to the inventive method essentially eliminates or substantially reduces the risk of damage being caused to the implant by an immune reaction of the patient, and thereby essentially eliminates or substantially reduces the need for carrying out a repetitive operation or repair operation. Additionally, the number and the dosage of conventionally administered drugs for suppressing the immune reaction and the like can be considerably reduced, whereby the number and the extent of side effects are consequently reduced. As a result, the quality of life of the respective affected patient is improved, while simultaneously the costs of the medical treatment can be reduced.

The method according to the invention may be carried out in either of two alternative operating modes, namely a so-called stepper mode and a so-called centrifuge mode. Each of these two modes respectively has its own special characteristics. The stepper mode provides for successive intermittent partial rotations with a freely selectable rotational angle and sedimentation pauses at each respective angular position. In this mode, it is possible to deposit a respective cell deposition or colonization line onto a respective line area of the surface of the implant, whereupon successive cell deposition or colonization lines deposited during the successive sedimentation pauses over the course of several complete rotations of the receiving container are joined or united together to form an overall uniform surface-coating colonization layer of the cells.

On the other hand, in the centrifuge mode, a continuous rotation of the receiving container exerts a centrifugal force onto the cells, such that the centrifugal force presses the cells uniformly against the intended surface or surfaces of the implant. In this context, the centrifugal force is maintained at a level high enough to achieve the desired deposition of the cells, but below a critical limit, for example 500 G (whereby "G" is the earth's gravitational acceleration), so that the living cells are effectively pressed against the implant surface without being ruptured or otherwise disrupted or destroyed.

In order to carry out the inventive method, the implant that is to be coated is first placed into a fitting receiving container of the coating apparatus. This receiving container ensures that a defined quantity of the nutritive biological liquid medium containing a defined number of living cells can be applied onto the surface or surfaces of the implant. Moreover, this arrangement ensures that the implant exactly follows, i.e. carries out, the automated rotations that are applied by the coating apparatus to the receiving container. In other words, there shall be no play or looseness of the implant within the receiving container. In this manner it is also ensured that the implant is adequately supported and does not change its position during the coating process, and that the implant is not inadvertently fractured or crushed or otherwise disrupted during the coating process, for example as a result of being thrown about within the receiving container during the relatively high rotational speeds that can be used during the coating process.

BRIEF DESCRIPTION OF THE DRAWINGS

In order that the invention may be clearly understood it will now be described in connection with an example embodiment, with reference to the accompanying drawings, wherein.

DETAILED DESCRIPTION OF PREFERRED EXAMPLE EMBODIMENTS AND OF THE BEST MODE OF THE INVENTION

Figure 1:
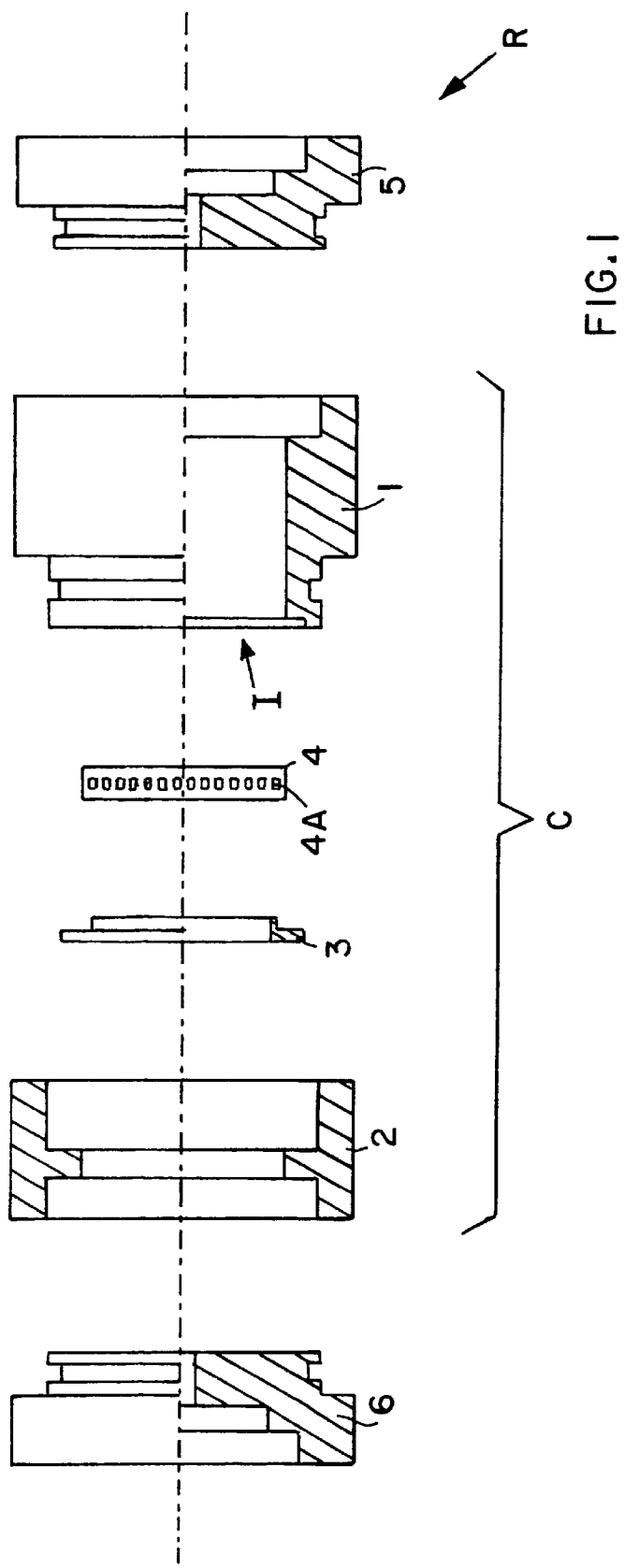
FIG. 1 is an exploded view, partially in section, of a receiving container for receiving a medical implant that is to be surface coated according to the invention.

The receiving container R shown in an exploded or disassembled manner in FIG. 1 is made of a biologically inactive and inert, synthetic plastic material, which can be steam sterilized at a temperature of 121° C. and which maintains its form stability under such conditions. The receiving container R essentially comprises a cylinder C in which a medical implant, such as a heart valve or the like, can be received and secured. The cylinder C comprises and is formed by two generally cylindrical parts, namely a valve carrier 1 and a connecting member 2, which are plugged together with a flat ring 3 (e.g. of stainless steel), received in a groove or recess therebetween. A lip 4 having regularly spaced or distributed bores or holes 4A around the circumference thereof is carried on the flat ring 3, and serves to help secure the heart valve or other implant in the internal chamber I formed within the cylinder C, while still allowing the liquid medium to circulate freely through the holes 4A.

The cylinder C is then closed respectively at its top and bottom ends by respective top and bottom lids or covers 5 and 6 that are plugged into corresponding recesses provided in the open ends of the valve carrier 1 and the connecting member 2 respectively. The lids 5 and 6 each have a central bore or a milled opening for receiving a plug-in filter with a so-called Luer-Lock connector. These filters are semipermeable and allow gases to be removed from or introduced into the interior chamber I within the cylinder C, without allowing the liquid present in the chamber I of the cylinder to escape. The several connections of the separate components of the receiving container R, and particularly the connections between the valve carrier 1 and the connecting member 2 as well as the respective connections with the lids 5 and 6, are sealed in any conventionally known manner, for example using O-ring seals made of silicone rubber, which are also suitable for being steam sterilized at a temperature of 120° C.

Figure 2:
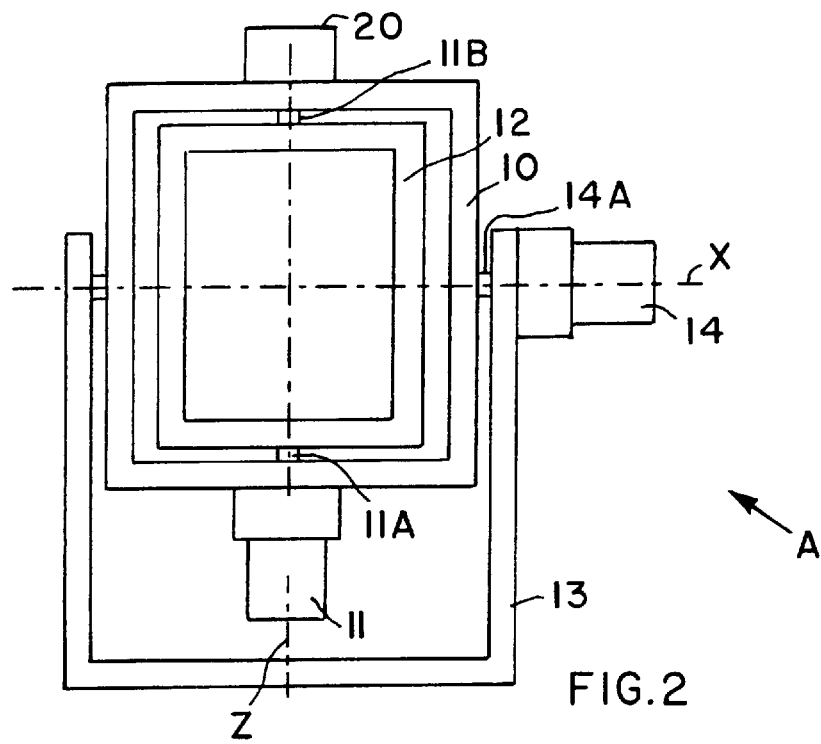
FIG. 2 is a schematic illustration of an apparatus for carrying out the coating of implants according to the invention, in an initial or starting position of the apparatus.
Figure 3:
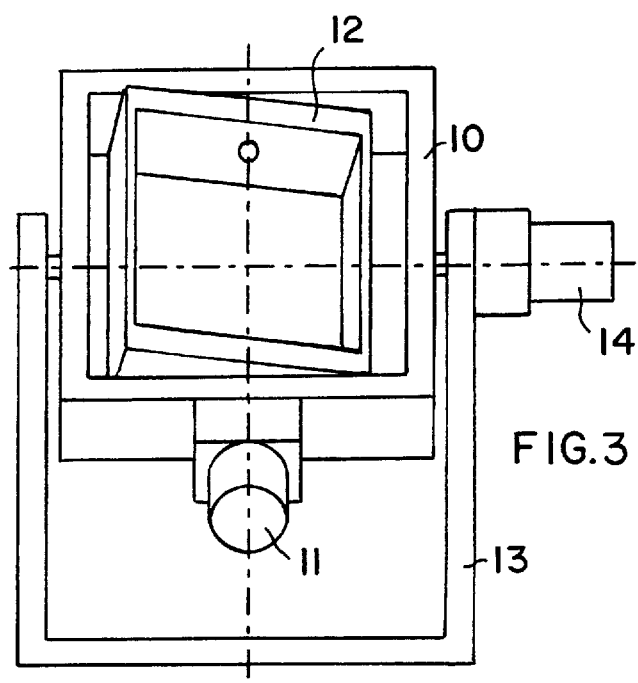
FIG. 3 is a schematic view of the apparatus according to FIG. 2, but shown in a momentary position during a coating process.

A plurality of different sizes of receiving containers R, or particularly different sizes of valve carriers 1, and if necessary different sizes of connecting members 2, and lids 5 and 6 are provided to make it possible to coat different sizes of medical implants according to the inventive method. Thus, a particular receiving container R having an appropriate chamber diameter and chamber height therein can be selected to securely receive any particular medical implant therein. In other words, the size of the receiving container R is selected depending on the dimensions of the medical implant that is to be received therein. In any event, the several different sizes of receiving containers R all have an external configuration so that they may be mounted into a coating rotator apparatus A shown in FIGS. 2 and 3, regardless of the particular size of the chamber I provided inside the respective receiving container R.

The coating rotator apparatus A comprises a rectangular outer frame 10 which has an elongated rectangular shape extending along a Z-axis in the illustrated embodiment. A rotational drive unit 11, preferably a stepper motor 11, is mounted on one end of the outer frame 10 so that the rotation axis of the shaft 11A of the drive unit 11 coincides with the Z-axis. The coating rotator apparatus A further comprises an inner frame 12 that is rotatably arranged within the outer frame 10. Specifically, the inner frame 12 includes two frame members extending substantially parallel to the Z-axis, interconnected by two crosswise members that extend perpendicularly to and intersect the Z-axis. One of the crosswise members of the inner frame 12 is secured to the drive shaft 11A of the rotational drive unit 11, for example by a set screw or the like, while the other one of the crosswise members of the inner frame 12 is freely rotatably supported relative to the opposite side of the outer frame 10, for example by an oil-lubricated brass guide or bearing sleeve.

Either the frame members or the crosswise members of the inner frame 12 comprise cap members that are turned or otherwise formed from aluminum or the like, and are adapted to securely reach over or snap onto the lids 5 and 6 of a receiving container C so as to securely hold the receiving container therebetween. Moreover, the cap members may exert a clamping effect, or may otherwise be secured, for example by a cam or a catch or the like, onto the lids of the receiving container. Preferably, the receiving container is received in the inner frame 12 so that a longitudinal axis of the container coincides with the rotation axis Z, while a crosswise axis of the container coincides with the rotation axis X. Instead of a complete rectangular inner frame 12, the frame members parallel to the Z-axis can be omitted and the container may simply be directly held and secured by the cap members extending parallel to the X-axis for rotation about the Z-axis.

With the above described arrangement, the inner frame 12 carrying the receiving container C can be rotated about the Z-axis by actuating the drive unit 11 as will be described below. Moreover, the outer frame 10 carrying the inner frame 12 can be rotated about the X-axis that is substantially perpendicular to the Z-axis by means of the following arrangement. To achieve this, the outer frame 10 is supported in a support yoke 13 so as to be rotatable relative to the support yoke 13 about the X-axis. A second rotational drive unit 14 such as a stepper motor 14 is mounted on one yoke arm of the support yoke 13 so that the shaft 14A of the stepper motor 14 is coaxially aligned on the X-axis. One side of the outer frame 10 is secured to this shaft 14A, while the other side of the outer frame 10 is freely rotatably supported relative to the support yoke 13.

The support yoke 13 has a relatively high mass and is sufficiently strong and stable so as to withstand the vibrations and any instabilities that arise during the rotational operation of the apparatus. Moreover, counterbalance weights may be arranged on the apparatus to minimize any out-of-balance rotational conditions. For example, a counterbalance weight 20 is schematically illustrated, mounted on the outer frame 10 at a location opposite the drive unit 11.

The two drive units 11 and 14 are embodied or adapted as needed for carrying out either or both of a continuous rotation of the inner frame 12 about the Z-axis and of the outer frame 10 about the X-axis with freely selectable rotational speeds, and/or stepwise or intermittent partial rotations through successive angular steps having a freely selectable angular step size or range. Moreover, the drive units 11 and 14 can be actuated independently so as to carry out rotations simultaneously or separately and successively with respect to each other. The drive units 11 and 14 of the coating rotator apparatus A are actuated and controlled by an external control electronics, which may be operated via a personal computer, for example.

For carrying out a coating process, various different operating modes of the coating rotator apparatus are available, by appropriately actuating the drive units 11 and 14 by means of the control electronics. For example, in a stepper mode, one or both of the drive units 11 and 14 are operated to carry out stepwise partial rotations through a freely selectable rotational angle that can be selected by the control electronics. The receiving container that is mounted in the inner frame 12 is thereby rotated stepwise about the respective axis or axes to successive angular positions at which the rotation is stopped for a freely selectable time period. Each such stopped time period represents a sedimentation pause in which gravity causes a sedimentation of the cells out of the liquid suspension and onto the surface of the medical implant. The sedimentation of the cells successively coats separate areas of the surface of the medical implant respectively during the successive sedimentation pauses at different rotational positions of the receiving container. The total duration of this stepper mode of operation is also freely selectable by means of the control electronics. In order to ensure that cells that have already been deposited and colonized as a coating on the surface of the medical implant are not irritated or disrupted and thereby dislodged from the underlying surface due to a too-strong acceleration of the receiving container following a sedimentation pause, the rotational speed is also freely selectable, and is generally rather low to avoid sudden acceleration effects.

Since the rotation of the two drive units 11 and 14 about the two axes X and Z can be controlled fully independently, it is possible to achieve any desired combination of different rotation parameters about the two axes. It is particularly advantageous to provide a combination in which one of the two drive units 11 and 14 is actuated to rotate the receiving container about one of the two rotational axes in such a manner so that several cell deposition or colonization points are successively deposited along a single deposition or colonization line on the surface of the implant. Then a plurality of rotations are carried out in this manner, respectively with a certain offset relative to the preceding rotation. The second drive unit is temporarily actuated in order to adjust the receiving container rotationally about the second axis to establish a position for the next successive deposition or colonization line, and the above described process is repeated for the next successive colonization line. This sequence is repeated for successive colonization lines until the entire surface is uniformly coated with a layer of cells.

A second operating mode for either one or both of the drive units is a centrifuge operating mode. In this mode, the coating process is carried out with centrifugal forces acting on the cells, whereby the magnitude and direction of the centrifugal forces are dependent on at least the dimensions of the receiving container, the orientation and position of the implant within the receiving container, the orientation and securing of the receiving container relative to the rotational axes, and the rotational speed applied about the rotational axes. The generated centrifugal forces press the cells against the implant's lateral walls that are to be coated. When the receiving container is rotated about an axis, an oriented or directed force vector acts respectively on each cell of the homogeneous cell suspension and thereby drives each individual respective cell to a specific respective location. When a respective rotation is carried out simultaneously about the two axes X and Z, the resultant force vector that arises from the vector pair corresponding to the centrifugal force components relative to the two rotation axes will have a resultant combined effect on the cells. By properly combining rotations about the two axes, it is possible to direct the resultant force vector in essentially any direction as needed to effectively coat an implant surface having any configuration or orientation. In this context, the magnitude of the centrifugal force should not exceed a prescribed limit or threshold value, for example 250 G, in order to prevent the cells from being ruptured or otherwise destroyed by excessive centrifugal forces.

A process for coating a heart valve or heart valve flaps can be carried out in the following manner, for example. First, the heart valve or heart valve flap is inserted into and secured in the inner chamber of the receiving container, which is also at least partially filled with a nutritive liquid medium containing the desired cells in suspension. Next, the receiving container is mounted in the coating rotator apparatus.

The first rotation step is preferably a combined rotational motion of the receiving container (and the implant, cells, and liquid therein) about the two rotational axes. Specifically, a rotation about only the lengthwise axis is preferably carried out first for approximately 1 minute. Then a rotation about the crosswise axis is added so as to carry out a combined simultaneous rotation about the two axes. The entire running duration of this rotational step is approximately 15 minutes.

Following the above described first rotational step, the cell suspension contained in the receiving container is again homogenized and then a rotation about only the crosswise axis is carried out, for approximately 15 minutes.

Next, a rotation step for coating the central portions of the heart valve flap pockets is carried out in a stepper mode. To achieve this, an intermittent or stepped rotational motion of the receiving container about only the crosswise axis is carried out. For example, this stepwise motion involves rotating the receiving container successively stepwise to three points around a complete circle, i.e. with 120° rotational angle steps, and a respective five minute sedimentation time for each deposition or colonization point. Next, the receiving container is rotated about the lengthwise or longitudinal axis through a rotation angle that has been previously specified dependent on the valve position (e.g. 40°), and then the preceding step of rotation about the crosswise axis is repeated.

A particular application example of the inventive method for coating a heart valve of the aorta or pulmonary positions will be described in detail. This heart valve may either be an artificial synthetic heart valve, or a commercially available biological heart valve or heart valve flap, for example a heart valve or flap that has been harvested from a donor animal a short time before the coating procedure.

In order to carry out the coating, approximately 40,000 cells are used per each square centimeter of the heart valve surface that is to be coated. For the cell pool, it is possible to use commercially available cell lines, or self-developed or generated cell lines, which are preferable. For this purpose, a piece of blood vessel approximately 5 cm long is explanted from the recipient patient, for example from the vena saphena magna, the vena basilica or the vena cephalica. Using an enzyme, for example typically collagenase, the endothelial cells are dissolved or separated out of the collagen matrix and are extracted with a flushing medium. This suspension is then fractionated and the desirable fraction is filled into culture flasks. While maintaining proper incubation conditions, the cell population is regularly monitored, and filled into larger culture flasks as needed, until a sufficient number of cells for coating the required surface area of a heart valve is available.

In order to prepare for the subsequent coating process, the heart valves or flaps are rinsed and flushed, for example in phosphate buffered saline (PBS), and then treated further depending on their origin. The surfaces of synthetic or artificial heart valves that are to be coated with cells are first treated with a fibrin adhesive to form a submatrix on which a one-layered cell coating, in this case consisting of endothelial cells, can establish itself. Commercial biological heart valves or flaps are typically supplied in a glutaraldehyde preservation solution and are first rinsed in an amino acid bath such as L-glutamine for example, and are then detoxified by removing the aldehyde groups. Next, the surfaces to be coated are treated with fibronectin, a high molecular weight protein body (e.g. molecular weight of approximately 450,000). The fibronectin binds itself with the cell surfaces and also with the intracellular structures, for example the collagen fibers, onto which the cells used for forming the coating are fixed in vivo. In this manner, a submatrix is formed, on which a single-layered coating of endothelial cells can be grown.

Heart valves or flaps explanted out of donor animals and not pre-treated in any manner naturally still have their own endothelial layer specific to the particular donor animal. In order to remove this endothelial layer, after first flushing or rinsing the heart valve, a de-endothelialization is carried out. This is achieved, for example, by using a biological detergent, such as deoxycholic acid. After further flushing or rinsing, fibronectin is once again utilized in order to facilitate the establishment of a single-layered coating of the recipient patient's endothelial cells on the surfaces of the implants.

The endothelialization, i.e. formation of an endothelial layer of the recipient patient's cells, in the above described manner is carried out in an incubator in which the entire coating rotator apparatus, the receiving container, and the heart valve implant contained therein, are held and maintained at about 37° C. (e.g. +/−1° C.) in a 5% carbon dioxide atmosphere and/or with at least about 95% (e.g. +/−2%) or for example 98% relative humidity. Thereafter, the receiving container is removed from the coating rotator apparatus and the remaining cell suspension which contains non-adherent cells or dead cells is sucked out of the chamber of the receiving container. Then the receiving container is refilled with fresh nutrient medium and once again arranged in the incubator. A further incubation period may then be carried out so that any possible remaining holes or gaps in the cell layer can be filled by further cell growth, up to the point of complete and uniform coating, i.e. confluence of the cell coating layer on the surfaces of the implant. The nutritive medium is exchanged at regular intervals, for example approximately every second day, during an incubation time of approximately one week. Thereafter, the coated heart valve can be removed from the receiving container and is ready to be implanted into the recipient patient.

Although the invention has been described with reference to specific example embodiments, it will be appreciated that it is intended to cover all modifications and equivalents within the scope of the appended claims. It should also be understood that the present disclosure includes all possible combinations of any individual features recited in any of the appended claims.

What is claimed is:

1. A method of coating a surface of a medical implant with a coating layer of living cells, comprising the following steps:

a) placing a medical implant into a chamber of a receiving container;

b) at least partially filling said chamber of said receiving container with a nutritive liquid having living cells in said liquid; and c) rotating said receiving container, which contains said medical implant, said liquid and said cells, simultaneously and independently about two distinct rotation axes;

so as to deposit a coating layer of said cells onto a surface of said implant.

2. The method according to claim 1, wherein said rotation axes intersect each other.

3. The method according to claim 2, wherein said rotation axes are substantially perpendicular to each other.

4. The method according to claim 1, wherein said placing of said medical implant into said chamber comprises inserting and securing said medical implant into said chamber.

5. The method according to claim 1, wherein said rotating comprises a continuous rotating including a plurality of continuously successive full rotations of said receiving container about at least one of said rotation axes.

6. The method according to claim 5, wherein said continuous rotating includes a plurality of continuously successive full rotations of said receiving container respectively about both of said rotation axes.

7. The method according to claim 1, wherein said rotating comprises an intermittent discontinuous rotating including a plurality of discontinuously successive partial rotations of said receiving container through respective rotation angles of less than 360° about at least one of said rotation axes.

8. The method according to claim 7, wherein said rotating additionally comprises, in combination with said intermittent discontinuous rotating, a continuous rotating including a plurality of continuously successive full rotations of said receiving container about at least one of said rotation axes.

9. The method according to claim 8, wherein said intermittent discontinuous rotating is carried out about a first one of said rotation axes, and simultaneously therewith said continuous rotating is carried out about a second one of said rotation axes.

10. The method according to claim 8, wherein said intermittent discontinuous rotating and said continuous rotating are carried out, in succession one after another, about the same one of said rotation axes.

11. The method according to claim 8, wherein said continuous rotating is carried out first, and then said intermittent discontinuous rotating is carried out.

12. The method according to claim 11, wherein said continuous rotating is carried out about both of said rotation axes for a time period of about five minutes.

13. The method according to claim 7, wherein said rotation axes respectively coincide with a longitudinal axis and a crosswise axis of said receiving container, and wherein said intermittent discontinuous rotating is carried out about said crosswise axis and said respective rotation angles are each rotation angles of 120° about said crosswise axis.

14. The method according to claim 13, wherein said intermittent discontinuous rotating further includes respective pauses between said successive partial rotations, and each one of said pauses has a duration of about five minutes.

15. The method according to claim 7, wherein said rotation axes respectively coincide with a longitudinal axis and a crosswise axis of said receiving container, and wherein said intermittent discontinuous rotating is carried out about said longitudinal axis and said respective rotation angles are each rotation angles of 40° about said longitudinal axis.

16. The method according to claim 15, wherein said intermittent discontinuous rotating further includes respective pauses between said successive partial rotations, and each one of said pauses has a duration of about two minutes.

17. The method according to claim 1, wherein said rotating is carried out for two different lengths of time respectively about said two rotation axes.

18. The method according to claim 1, further comprising, after completion of said rotating, another step of maintaining said receiving container with said implant, said liquid and said cells therein at a temperature of about 37° C. for a specified holding time.

19. The method according to claim 18, wherein said holding time has a duration of about seven days.

20. The method according to claim 18, further comprising supplying carbon dioxide gas into said chamber of said receiving container at least during said holding time.

21. The method according to claim 18, further comprising maintaining a relative humidity of about 95% in said chamber of said receiving container at least during said holding time.

22. The method according to claim 1, wherein said rotating is adapted to cause said cells to settle out of said liquid onto said surface of said implant under the effect of gravity.

23. The method according to claim 1, wherein said rotating is adapted to cause said cells to settle out of said liquid onto said surface of said implant under the effect of a centrifugal force arising as a result of said rotating.

* * * * *

UNITED STATES PATENT AND TRADEMARK OFFICE
CERTIFICATE OF CORRECTION

PATENT NO.     : 6,214,407 B1                                                Page 1 of 1
DATED          : April 10, 2001
INVENTOR(S)    : Laube et al.

It is certified that error appears in the above-identified patent and that said Letters Patent is hereby corrected as shown below:

<u>Title page,</u>
Item [73], Assignee, replace "co.don AG, DE" by -- co.don AG, Teltow, DE --.

Signed and Sealed this

Twenty-fifth Day of June, 2002

*Attest:*

JAMES E. ROGAN
*Attesting Officer*          *Director of the United States Patent and Trademark Office*